(12) United States Patent
Augustine et al.

(10) Patent No.: US 11,425,796 B2
(45) Date of Patent: Aug. 23, 2022

(54) CONFORMABLE HEATING BLANKET

(71) Applicant: Augustine Temperature Management LLC, Eden Prairie, MN (US)

(72) Inventors: Scott D. Augustine, Deephaven, MN (US); Randall C. Arnold, Minnetonka, MN (US)

(73) Assignee: Augustine Temperature Management, LLC, Eden Prairie, MN (US)

( * ) Notice: Subject to any disclaimer, the term of this patent is extended or adjusted under 35 U.S.C. 154(b) by 618 days.

(21) Appl. No.: 14/255,612

(22) Filed: Apr. 17, 2014

(65) Prior Publication Data

US 2014/0316494 A1 Oct. 23, 2014

Related U.S. Application Data

(60) Provisional application No. 61/812,987, filed on Apr. 17, 2013.

(51) Int. Cl.
| | |
|---|---|
| *A61F 7/00* | (2006.01) |
| *H05B 3/34* | (2006.01) |
| *B32B 27/12* | (2006.01) |
| *H05B 3/12* | (2006.01) |
| *H05B 3/14* | (2006.01) |

(Continued)

(52) U.S. Cl.
CPC ........... *H05B 3/342* (2013.01); *A47C 21/048* (2013.01); *A61F 7/007* (2013.01); *A61F 7/0097* (2013.01); *A61F 7/08* (2013.01); *A61G 13/10* (2013.01); *B32B 27/12* (2013.01); *H05B 3/12* (2013.01); *H05B 3/145* (2013.01); *H05B 3/146* (2013.01); *H05B 3/347* (2013.01); *A61F 2007/0071* (2013.01); *A61F 2007/0095* (2013.01); *A61F 2007/0098* (2013.01); *A61G 13/126* (2013.01); *A61G 2210/90* (2013.01); *B32B 2274/00* (2013.01); *B32B 2307/202* (2013.01); *B32B 2307/7265* (2013.01); *B32B 2439/00* (2013.01); *H05B 2203/013* (2013.01);

(Continued)

(58) Field of Classification Search
CPC .. A61F 2007/0098; A61F 7/0097; A61F 7/08; H05B 3/342; H05B 2203/016
See application file for complete search history.

(56) References Cited

U.S. PATENT DOCUMENTS 2,635,175 A * 4/1953 Hodge .................... A61F 7/007
219/528
2,715,674 A 8/1955 Abbott et al.
(Continued)

FOREIGN PATENT DOCUMENTS

WO 9923992 A1 5/1999
WO 01095841 A2 12/2001
(Continued)

*Primary Examiner* — Kaitlyn E Smith
*Assistant Examiner* — Yasamin Ekrami
(74) *Attorney, Agent, or Firm* — Fredrikson & Byron, P.A.

(57) ABSTRACT

Embodiments include a heating blanket. The heating blanket may include a heating element and a shell covering the heating element. The heating element has elastic properties and is disposed in the shape of a sheet. The shell may have one or more sheets of polymeric material bonded together adjacent a perimeter of the heating element. One or more wires having malleable properties are secured within the shell. The wires allow the heating blanket to be secured to a patient.

24 Claims, 10 Drawing Sheets (51) Int. Cl.
  *A47C 21/04* (2006.01)
  *A61F 7/08* (2006.01)
  *A61G 13/10* (2006.01)
  *A61G 13/12* (2006.01)

(52) U.S. Cl.
  CPC .. *H05B 2203/016* (2013.01); *H05B 2203/029* (2013.01); *H05B 2203/036* (2013.01)

(56) References Cited

U.S. PATENT DOCUMENTS

| | | | |
|---|---|---|---|
| 3,582,456 | A | 6/1971 | Stolki |
| 3,780,262 | A | 12/1973 | Rudd |
| 3,808,403 | A | 4/1974 | Gunma et al. |
| 3,874,504 | A | 4/1975 | Verakas |
| 4,118,531 | A | 10/1978 | Hauser |
| 4,125,287 | A * | 11/1978 | Paulisch ............ B60N 2/242 248/429 |
| 4,423,308 | A | 12/1983 | Callaway et al. |
| 4,495,402 | A | 1/1985 | Burdick et al. |
| 4,941,961 | A | 7/1990 | Noguchi et al. |
| 5,023,433 | A | 6/1991 | Gordon et al. |
| 5,320,164 | A * | 6/1994 | Szczesuil ............ A41D 13/005 165/46 |
| 5,723,845 | A | 3/1998 | Partington et al. |
| 5,755,275 | A * | 5/1998 | Rose ............ A61F 7/02 165/171 |
| 5,835,983 | A * | 11/1998 | McMahen ............ A61F 7/007 219/527 |
| 5,881,410 | A | 3/1999 | Yamada |
| 5,932,129 | A | 8/1999 | Hyatt et al. |
| 6,038,722 | A | 3/2000 | Giori et al. |
| 6,084,217 | A | 7/2000 | Bulgajewski et al. |
| 6,189,487 | B1 | 2/2001 | Owen et al. |
| 6,210,427 | B1 | 4/2001 | Augustine et al. |
| 6,215,111 | B1 | 4/2001 | Rock et al. |
| 6,229,123 | B1 | 5/2001 | Kochman et al. |
| 6,240,623 | B1 | 6/2001 | Johansson et al. |
| 6,373,034 | B1 | 4/2002 | Rock et al. |
| 6,403,935 | B2 | 6/2002 | Kochman et al. |
| 6,416,534 | B1 | 7/2002 | Montagnino et al. |
| 6,434,328 | B2 | 8/2002 | Rutherford |
| 6,452,138 | B1 | 9/2002 | Kochman et al. |
| 6,452,139 | B1 | 9/2002 | Benoit et al. |
| 6,582,456 | B1 | 6/2003 | Hand et al. |
| 6,770,854 | B1 | 8/2004 | Keane |
| 6,872,758 | B2 | 3/2005 | Simpson et al. |
| 6,933,469 | B2 | 8/2005 | Ellis et al. |
| 6,967,309 | B2 | 11/2005 | Wyatt et al. |
| 7,053,344 | B1 | 5/2006 | Surjan et al. |
| 7,161,120 | B1 | 1/2007 | Stroud et al. |
| 7,176,419 | B2 | 2/2007 | Ellis et al. |
| 7,375,308 | B2 | 5/2008 | Ferguson |
| 7,543,344 | B2 | 6/2009 | Augustine et al. |
| 7,673,356 | B1 * | 3/2010 | Conyers ............ A45D 44/10 4/572.1 |
| 7,714,255 | B2 | 5/2010 | Augustine et al. |
| 7,851,729 | B2 | 12/2010 | Augustine et al. |
| 8,065,763 | B2 | 11/2011 | Brykalski et al. |
| 8,283,602 | B2 | 10/2012 | Augustine et al. |
| 8,288,693 | B2 | 10/2012 | Weiss et al. |
| 8,291,612 | B2 | 10/2012 | Ferguson |
| 8,418,297 | B2 | 4/2013 | Mikkelsen et al. |
| 8,624,164 | B2 | 1/2014 | Deibel et al. |
| 8,698,044 | B2 | 4/2014 | Burr et al. |
| 2001/0020303 | A1 | 9/2001 | Endo et al. |
| 2002/0124312 | A1 | 9/2002 | Yoon |
| 2002/0133213 | A1 * | 9/2002 | Tippitt ............ A61F 7/007 607/98 |
| 2004/0149711 | A1 | 8/2004 | Wyatt et al. |
| 2004/0164499 | A1 | 8/2004 | Murakami et al. |
| 2004/0174056 | A1 | 9/2004 | Gryp et al. |
| 2004/0237206 | A1 | 12/2004 | Webster et al. |
| 2005/0016982 | A1 | 1/2005 | Campf et al. |
| 2005/0194089 | A1 * | 9/2005 | Phillips ............ H01L 51/0013 156/227 |
| 2006/0138832 | A1 * | 6/2006 | Ogura ............ B60N 2/66 297/284.4 |
| 2006/0260060 | A1 | 11/2006 | Apperson et al. |
| 2006/0261055 | A1 * | 11/2006 | Child ............ H05B 3/342 219/212 |
| 2007/0068930 | A1 | 3/2007 | Augustine et al. |
| 2007/0108190 | A1 | 5/2007 | Ferguson |
| 2007/0152479 | A1 | 7/2007 | Howman et al. |
| 2007/0164010 | A1 | 7/2007 | Rock et al. |
| 2007/0272673 | A1 | 11/2007 | Keane |
| 2008/0173629 | A1 | 7/2008 | Deibel et al. |
| 2008/0203080 | A1 | 8/2008 | Fung |
| 2008/0230530 | A1 * | 9/2008 | Augustine ............ H05B 1/0272 219/212 |
| 2008/0255641 | A1 | 10/2008 | Ellis |
| 2008/0283513 | A1 | 11/2008 | Ferguson, III et al. |
| 2009/0078690 | A1 | 3/2009 | Lee et al. |
| 2009/0095735 | A1 | 4/2009 | Resheff |
| 2009/0099631 | A1 * | 4/2009 | Augustine ............ A61F 7/007 607/104 |
| 2009/0222996 | A1 | 9/2009 | Balonick et al. |
| 2010/0078807 | A1 * | 4/2010 | Schulz ............ H01L 23/34 257/713 |
| 2010/0119704 | A1 | 5/2010 | Hemmelgarn et al. |
| 2010/0161016 | A1 | 6/2010 | Augustine et al. |
| 2010/0200558 | A1 * | 8/2010 | Liu ............ H05B 3/342 219/212 |
| 2010/0204763 | A1 | 8/2010 | Augustine et al. |
| 2010/0224612 | A1 | 9/2010 | Asami et al. |
| 2010/0279086 | A1 | 11/2010 | Park et al. |
| 2010/0283295 | A1 | 11/2010 | Smith et al. |
| 2010/0325796 | A1 | 12/2010 | Lachenbruch et al. |
| 2011/0031230 | A1 | 2/2011 | Kim |
| 2011/0099900 | A1 * | 5/2011 | Weder ............ A47G 7/085 47/66.7 |
| 2012/0111846 | A1 | 5/2012 | Hammerschmidt |
| 2012/0273475 | A1 | 11/2012 | An |
| 2012/0279953 | A1 | 11/2012 | Augustine et al. |
| 2013/0110022 | A1 * | 5/2013 | Meals ............ A61F 5/0118 602/20 |
| 2013/0116762 | A1 * | 5/2013 | Lai ............ A61F 7/10 607/109 |
| 2014/0074086 | A1 | 3/2014 | MacIntyre-Ellis et al. |
| 2014/0173799 | A1 * | 6/2014 | VanErmen ............ A41D 19/0096 2/2.5 |

FOREIGN PATENT DOCUMENTS

| | | |
|---|---|---|
| WO | 2007041389 A1 | 4/2007 |
| WO | 2010107724 A1 | 9/2010 |

* cited by examiner

CONFORMABLE HEATING BLANKET

PRIORITY

This application claims priority to U.S. Provisional Application No. 61/812,987, Flexible Electric Heaters, filed on Apr. 17, 2013, the disclosure of which is hereby incorporated by reference in the entirety.

FIELD

This disclosure generally relates to heating or warming blankets or pads and more particularly to those including electrical heating elements.

BACKGROUND

Surgical patients under anesthesia may become poikilothermic. In such cases, patients may lose their ability to control their body temperature and can take on or lose heat depending on the temperature of the environment. Since modern operating rooms are typically air conditioned to a relatively low temperature and optimized for surgeon comfort, patients undergoing general anesthesia may lose heat and become clinically hypothermic if not warmed.

Electric warming blankets have been used to warm patients during surgery. The heating blankets used in the operating room may be made of multiple layers of materials including fabrics, plastic film and fibrous non-woven materials. These layers may be bonded together into laminated structures. These multiple layer constructions may result in blankets that may not offer adequate flexibility. Such heating blankets may not naturally drape over the patient and may not make good contact with the patient's sides to maximize the surface area available for conductive heat transfer. Further the blankets are typically secured to the patient so that they do not fall off during surgery. Such blankets are secured and maintained in position by adhesive tape or hook-and-loop straps.

It is often the case that the patient is positioned horizontally in the surgery room. In such cases, the blanket is held in place by gravity. However, this orientation may be changed. For instance, the patient may be positioned upright (e.g., vertically standing). In these situations, it may not be possible for the heating blanket to be placed on the top surface of the patient and held in place by gravity. In some cases, the blanket may be wrapped around the supine patient's head.

SUMMARY OF THE INVENTION

Certain embodiments of the invention include a heating blanket. The heating blanket may include a heating element having elastic properties and disposed in the shape of a sheet. The heating element may have a perimeter. A shell may cover the heating element. The shell can include at least a first sheet and a second sheet of polymeric material having elastic properties. The shell can have a perimeter. A first weld can couple the first and second sheets of polymeric material together adjacent the first perimeter of the heating element. A plurality of wires may be secured within the heating blanket. Each of the plurality of wires can have malleable properties to allow the heating blanket to be secured to a patient.

In some embodiments, the heating blanket may include a second bond formed between the first sheet and the second sheet of polymeric material, adjacent the perimeter of the shell and parallel to the first bond. The second bond may define an elongate sheath along at least an edge of the shell. In such embodiments, the plurality of wires is inserted into the elongate sheath before sealing an end of the elongate sheath shut. The first and second bonds may be disposed on the heating blanket such that at least the first sheet of the polymeric material extends beyond the first bond. The first sheet may then be wrapped back and bonded to itself to form the elongate sheath adjacent the second perimeter of the shell. A strip of polymeric film or fabric is then bonded with the first and second bonds to secure the strip of polymeric film at the edge of the shell. This may alternatively form the elongate sheath adjacent the second perimeter of the shell into which the plurality of wires is inserted before sealing the end of the elongate sheath shut. One or more tubes may be inserted into the elongate sheath before sealing an end of the elongate sheath shut to form a rounded edge.

BRIEF DESCRIPTION OF THE DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments may include aspects of patient warming systems as disclosed in U.S. patent application Ser. No. 13/422,279, Heated Under-body Warming Systems, and U.S. Pat. No. 8,283,602, Heating Blanket, the disclosures of each of which are hereby incorporated by reference in their entirety. For example, in some cases, the heating blanket can be sized and shaped for the upper body or upper body limb (e.g., a wrap-around blanket), or sized and shaped for the lower body or lower body limb. In some cases the heating blanket can be used in conjunction with a disposable cover. Such embodiments may offer improved contact between the blanket and the patient, resulting in better heat transfer from the blanket to the patient.

Figure 1:
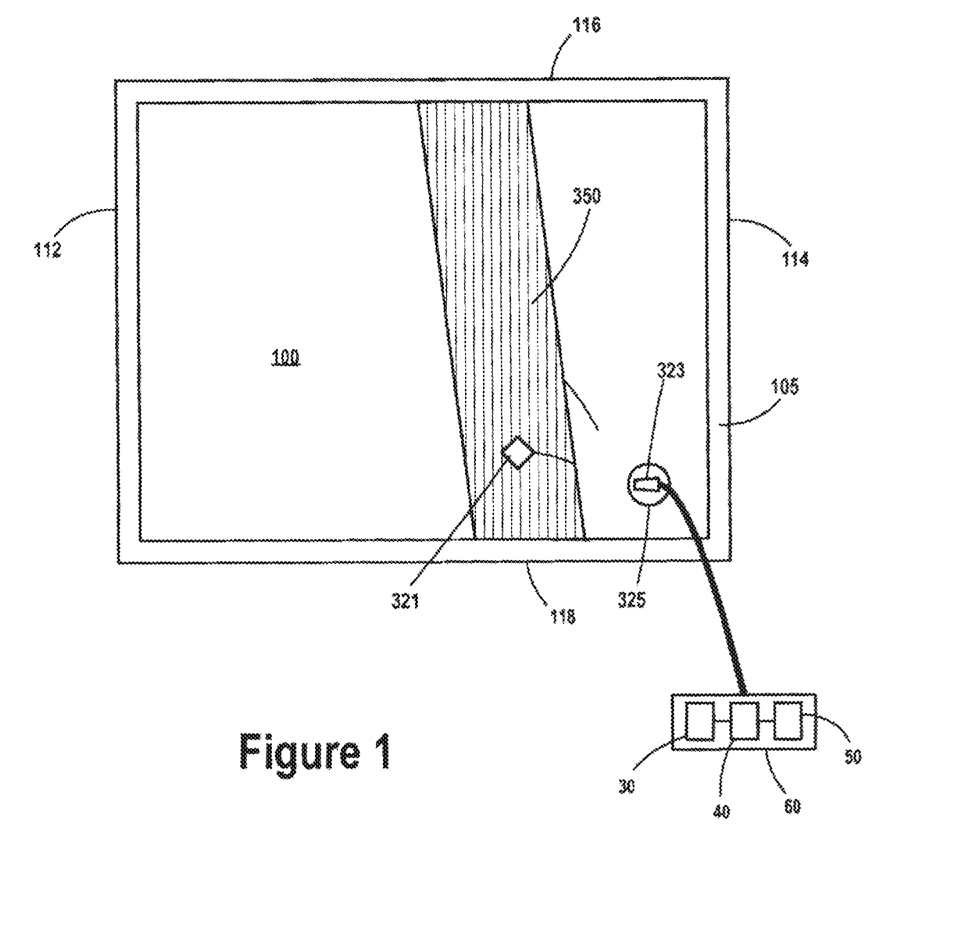
FIG. 1 is a top plan view of a heating blanket, according to some embodiments of the present invention.

FIG. 1 shows a heating blanket 100 according to some embodiments of the invention. As shown, the heating blanket 100 is generally rectangular. However, the shape of the heating blanket 100 is not limiting and the heating blanket 100 can be formed into any shape. As will be discussed herein, the heating blanket may include a heating element. The heating element may have elastic properties and can be disposed in the shape of a sheet. The heating element may be coupled to electrical terminals discussed in detail herein, to supply current. The heating element may have electrical resistance, which can be related to the heat generated by the heating element by the following relationship: $Q=I^2 \times R$, wherein Q indicates the heat generated in Joules, I indicates the current through the heating element in Amperes, and R indicates the electrical resistance of the heating element in Ohms.

In some embodiments, a shell may cover the heating element. As shown in FIG. 1, a portion of the shell 105 is cut away, revealing the heating element assembly 350. The heating element assembly 350 is generally covered by the shell and can extend within the shell 105 between edge 112 and edge 114 and between edge 116 and edge 118. The shell 105 can be liquid-proof. The shell 105 can protect and isolate the heating element assembly 350 from an external environment of heating blanket 100. The shell 105 can include a liquid-resistant material layer that can form a substantially hermetic seal around the heating element assembly 350. The shell 105 can provide further protection to a patient disposed beneath heating blanket 100 against electrical shock hazards. According to some embodiments of the present invention, shell 105 is liquid-proof to prevent fluids (e.g., bodily fluids, IV fluids, cleaning fluids, etc.) from contacting the heating element assembly 350. In some embodiments, shell 105 may further include an anti-microbial element such as ions coated or deposited on the shell 105 (e.g., an anti-microbial fabric such as SILVERion™ or Ultra-Fresh™).

The shell 105 may include one or more sheets of polymeric material. For instance, the shell may include a first sheet and a second sheet of polymeric material. The first and second sheets may have elastic properties. The shell may have a perimeter defined by one or more edges. According to an illustrative embodiment, the shell 105 comprises urethane or polyvinyl chloride (PVC) to facilitate a radiofrequency weld to bond the first and second sheets adjacent or along the perimeter. Other polymeric materials are also contemplated. For instance, the shell may include a polymer bonded to a fabric.

Figure 2A:
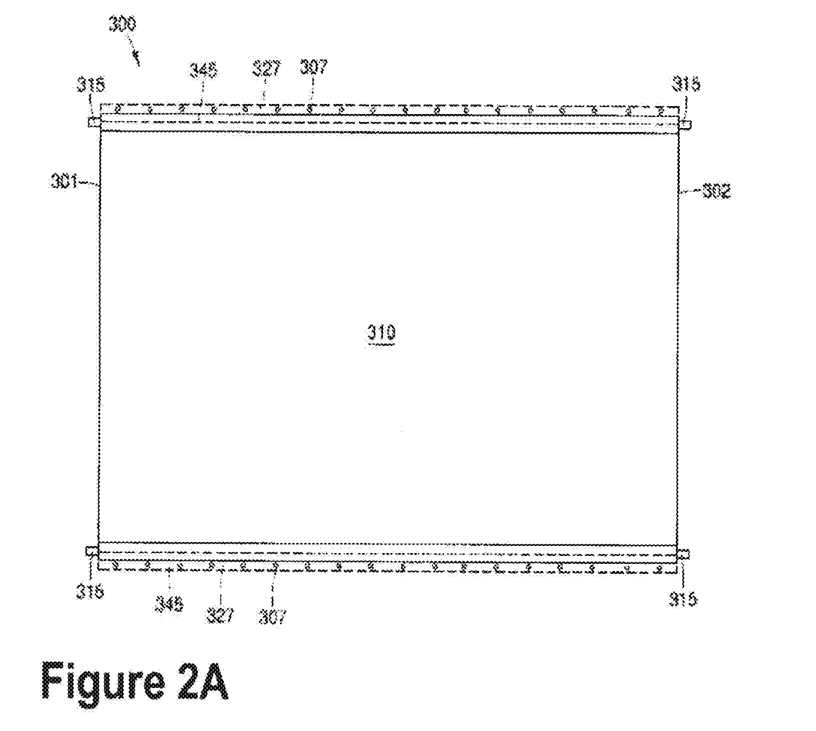
FIG. 2A is a plan view of a flexible heating blanket subassembly for a heating blanket, according to some embodiments of the present invention.
Figure 2B:
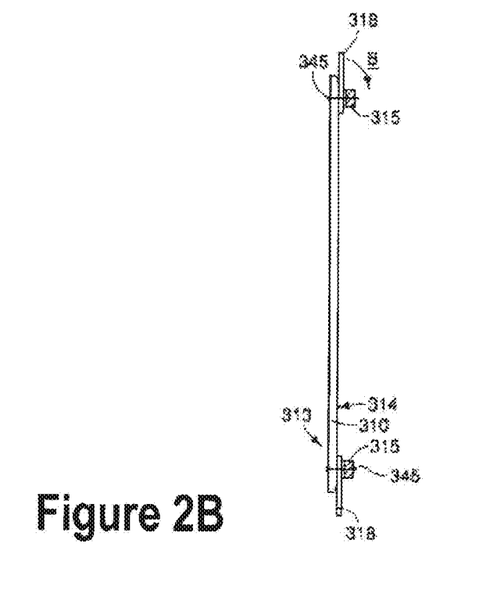
FIG. 2B is an end view of some embodiments of the subassembly shown in FIG. 2A.

In the illustrated embodiments seen in FIGS. 1-2B, the heating element is rectangular. However, any shape is contemplated. FIGS. 2A-2B show an illustrative heating blanket subassembly 300 that can be incorporated into heating element assemblies (e.g., heating element assembly 350 of FIG. 1) in some embodiments. The heating blanket subassembly 300 can be flexible (e.g., elastically stretchable). The heating blanket subassembly 300 can include a heating element 310. The heating element 310 can include a first edge 301 and a second edge 302, a third edge and a fourth edge. The first, second, third and fourth edges can be arranged to form a perimeter of the heating element.

With continued reference to FIGS. 2A-2B, the blanket subassembly 300 can allow the blanket 100 to conform to the contours of a body (e.g., all or a portion of a patient undergoing surgery). This ability to conform may be provided by the heating element 310 which may have elastic properties, and can be enhanced by providing electrical terminals with elastic properties. Conforming to the contours of a patient's body is preferable to simply bridging across high spots of the body. Such conformance may optimize a conductive heat transfer from heating element 310 to a surface of the patient's body.

In some embodiments, heating element 310 may include a conductive fabric or a fabric incorporating closely spaced conductive elements such that heating element 310 has desirable heat generation characteristics. The heat generation characteristics may be quantified by watt density output, or the amount of heat produced per unit area of the heating element. For instance, the heating element 310 may a substantially uniform watt density output. In some embodiments, the watt density output of the heating element 310 may be less than approximately 0.5 watts/sq. inch, or between approximately 0.2 and approximately 0.4 watts/sq. inch, across a surface area, of one or both sides 313, 314 of the heating element (FIG. 2B).

FIG. 2A further illustrates subassembly 300 including two electrical terminals 315 (e.g., electrical terminals) coupled to heating element 310 for powering heating element 310. An exemplary electrical terminal is described in U.S. Pat. No. 7,714,255, Bus Bar Attachments for Flexible Heating Elements, the disclosure of which is hereby incorporated by reference in its entirety. Each electrical terminal 315 is shown extending between first and second edges 301, 302. With reference to FIG. 2B, according to some embodiments, electrical terminals 315 are coupled to heating element 310 by sewing with electrically conductive thread (e.g., silver-coated polyester or nylon thread). Alternative threads or yarns may be made of other polymeric or natural fibers coated with other electrically conductive materials. In addition, nickel, gold, platinum and various conductive polymers can be used to make conductive threads. Metal threads such as stainless steel, copper or nickel could also be used for this application. The coupling of the electrical terminals 315 may form stitches 345. The conductive thread may have lower electrical resistance than the heating element and may not heat under normal conditions.

As shown in FIG. 2B, electrical insulation may be provided between the electrical terminals 315 and the heating element 310. FIG. 2B illustrates subassembly 300 wherein insulating members 318 (e.g. fiberglass strips, coated fiberglass strips with a PTFE coating) extend between electrical terminals 315 and heating element 310 at each stitch 345, so that electrical contact points between electrical terminals 315 and heating element 310 are defined by the stitches 345. Alternatively, the electrical insulation could be made of polymeric film, a polymeric film reinforced with a fibrous material, a cellulose material, a glass fibrous material, rubber sheeting, polymeric or rubber coated fabric or woven materials or any other suitable electrically insulating material. The thickness of the electrically insulating material can be approximately 0.003 inch. Alternatively, the thickness can be in the range of approximately 0.001 inch to 0.01 inch.

Each of the stitches 345 can maintain a stable and constant contact with the electrical terminal 315 on one side and heating element 310 on the other side of the insulating members 318. The stitches 345 can produce a stable contact in the face of flexion. Additionally, the stitches 345 may prevent intermittent contact between the electrical terminals 315 and heating element 310 that could potentially arise for embodiments in which the electrical terminal 315 is in physical contact with heating element 310.

According to an exemplary embodiment, electrical terminals 315 can be shaped as flattened tubes of braided wires, such as are known to those skilled in the art (e.g., a flat braided silver coated copper wire). Such embodiments may facilitate accommodation of the electrically conductive thread extending therethrough, passing through openings between the braided wires thereof. In addition such terminals may also have elastic properties. In alternate embodiments, electrical terminals 315 can be a conductive foil or wire, flattened braided wires not formed in tubes, patterned conductive thread, or a substrate coated with conductive ink. In some embodiments, electrical terminals 315 are each a flat braided silver-coated copper wire material. In other embodiments, tin-coated wire may be used instead. Silver coating has shown superior durability with repeated flexion, as compared to tin-coated wire, for example, and may be less susceptible to oxidative interaction with a polypyrrole coating of heating element 310 according to an embodiment described below. Additionally, an oxidative potential related to dissimilar metals in contact with one another is reduced if a silver-coated thread is used. While silver-coating offers desirable properties, the specific type of coating does not limit the scope of the invention and any coating (e.g., tin) may be used.

According to an exemplary embodiment, the heating element 310 may include a conductive or a semi-conductive fabric. Alternatively, the heating element 310 may include a conductive or semi-conductive film. Some examples of conductive fabrics which may be employed by embodiments include, but are not limited to, carbon fiber fabrics, fabrics made from carbonized fibers, conductive films, or woven or non-woven non-conductive fabric or film substrates coated with a conductive or semi-conductive material, (e.g., polypyrrole), carbonized ink, or metalized ink. In some embodiments, the conductive fabric is a polymeric fabric coated with a conductive or semi-conductive polymeric material such as polypyrrole. In addition, the heating element 310 may be made from a matrix of electrically resistant wire or metal traces attached to a fibrous or film material layer. Because the fabric may be made with mechanical properties that allow repeated flexing without undue mechanical stresses developing in the fabric. Such embodiments may eliminate the need for a lamination to provide support to the heating element.

In some embodiments, a thermally insulating layer can be positioned to optimize and provide a maximal amount of heat from the heating element assembly 350 to the patient. In such instances, a thermally insulating layer can help insulate the heating element assembly 350 from the environment and provide a more uniform temperature distribution. The thermally insulating layer can be positioned between the heating element assembly 350 and the layer of the shell 105 that does not contact the patient. Embodiments such as these can facilitate the heating element assembly 350 in generating a maximal amount of heat which is transferred to the patient and not to the surrounding environment.

To protect the heating element from moisture, liquids and to electrically insulate the heater from the user, a layer of elastic polymer ("elastomer") or thermoplastic elastomer (TPE), can be applied to one or both sides of the conductive fabric. Elastomers may have elastic or viscoelastic properties allowing the fabric to continue to stretch or flex when a person's weight acts on the fabric. Elastomers may include elastic materials such as rubber. Some exemplary elastomers include but are not limited to: polyisoprene, polychloroprene (Neoprene), isobutylene, isoprene, nitrile rubber, polyacrylic rubber, silicone rubber, fluorosilicone rubber, perfluoroelastomers and ethylene-vinyl acetate (EVA). Thermoplastic elastomers (TPE) include but are not limited to: thermoplastic rubbers, elastomeric alloys, thermoplastic polyurethanes, thermoplastic copolyesters, thermoplastic polyamides and polyolefin blends. In some embodiments, the elastomer is silicone-based rubber and it is applied in a very thin layer. In some embodiments, the thickness of the elastomer layer is less than approximately 0.01 inches (10 mil), or between about 0.002 inches and about 0.02 inches (2-20 mil), to preserve the elastic properties of the fabric of the heating element. Alternatively, moisture and/or liquid-resistant and electrically insulating layers can be made of plastic film and bonded to or extruded onto the fabric of the heating element. Elastic films such as polyvinylidene chloride or polyurethane can be provided, but other plastic films may also be used.

In an exemplary embodiment, the heating element 310 may include a non-woven polyester having a basis weight of approximately 170 $g/m^2$ and coated with polypyrrole. In some embodiments, the polyester may be coated entirely with polypyrrole. The coated fabric may have an average electrical resistance (e.g., determined with a four point probe measurement) of approximately 15 ohms per square inch. Such fabrics may produce a watt density of 0.2 to 0.4 watts/sq. in. for surface areas of heating element 310 having a width of in the range of approximately 19 inches to approximately 28 inches between the electrical terminals 315, when powered at about 48 volts. In some embodiments, the basis weight (or weight per unit area in units of grams per square meter) of the non-woven polyester may be chosen in the range of approximately 80-180 $g/m^2$. However, other basis weights may be engineered to operate adequately are therefore within the scope of the embodiments.

The electrical resistance of conductive fabrics may be tailored for different widths between electrical terminals. For instance, the electrical resistance may vary inversely with the width of the fabric between electrical terminals. Alternatively, or in addition, the electrical resistance may be varied by increasing or decreasing a surface area of the fabric that can receive the conductive coating. In some instances, this can be achieved by increasing or decreasing the basis weight of the nonwoven fabric. In certain embodiments, resistance of the conductive fabrics is generally uniform over the surface area. However, the resistance of conductive fabrics over different portions of the surface area may vary based on many conditions. A few exemplary conditions under which the resistance of portions of the fabric may vary are (a) variation in a thickness of a conductive coating, (b) variation within the conductive coating itself, (c) variation in effective surface area of the substrate which is available to receive the conductive coating, or (d) variation in the density of the substrate itself.

Variability in resistance could potentially translate into variability in heat generation, as the heat generation of the fabric is related to the electrical resistance as describe elsewhere herein, and variability in heat generation could then manifest as a variation in temperature. However, according to some embodiments of the present invention, which are employed to warm patients undergoing surgery, precise temperature control can be provided. Such temperature control can be achieved as shown in FIG. 3B and will be described below.

Figure 3A:
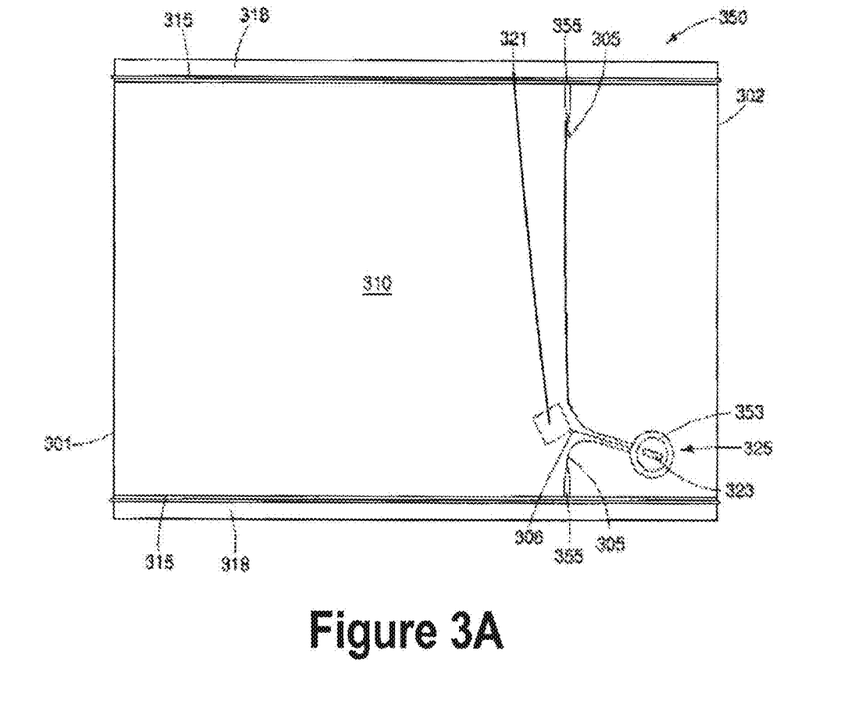
FIG. 3A is a top plan view of a heating element assembly, according to some embodiments of the present invention, which may be incorporated in the blanket shown in FIG. 1.
Figure 3B:
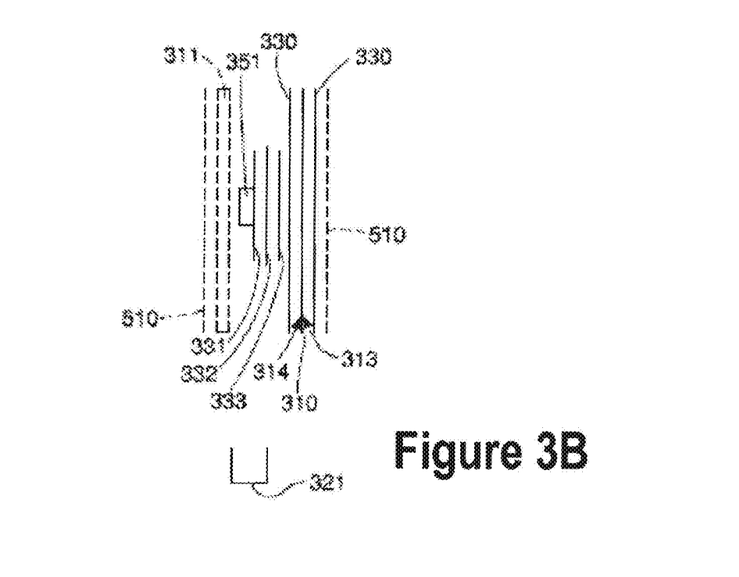
FIG. 3B is a section view of the temperature sensor assembly of FIG. 3A.

FIGS. 3A-3B show a heating element assembly 350 similar to the heating element assembly 350 of FIG. 1. The heating element assembly 350 can include a temperature sensor assembly 321. As seen in FIG. 1, an electrical connector housing 325 and a corresponding connector plug 323 can be coupled to the shell 105, thereby enabling access to a temperature sensor assembly such as those discussed below. Referring to FIG. 1, connector plug 323 can protrude from shell 105 of the heating blanket 100. An extension cable may couple the heating element assembly 350 to a console 60. The console 60 includes a shut-off timer 30 and a power source 50 each coupled to a control system (or controller) 40. The shut-off timer 30 can be operatively coupled to the control system 40, meaning that the shut-off timer 30 can be integrated into the control system 40, the shut-off timer 30 can be a separate component, or the shut-off timer 30 and the control system 40 can have any other suitable functional relationship. The temperature sensor assembly 321 can be configured to provide temperature information to the control system 40, which may act as a temperature controller. The controller may function to interrupt such power supply (e.g., in an over-temperature condition) or to modify the duty cycle to control the heating element temperature.

Referring back to FIGS. 3A-3B, the temperature sensor assembly 321 is coupled to heating element 310 at a location where heating element 310 may come into conductive contact with the patient. This can assist in maintaining a uniform temperature distribution across heating element 310. Such embodiments may improve reliability and safety by providing a controllable temperature. In some embodiments, the temperature sensor assembly 321 can be provided separately from the heating blanket.

In some embodiments, the temperature sensor 351 is positioned such that the regions surrounding sensor 351 may be in conductive contact with the body when a heating blanket is placed over a body. As previously described, in an exemplary situation, a temperature of approximately 43° C. be maintained over a surface of heating element 310 which is in conductive contact with a body of a patient undergoing surgery. An additional or alternate embodiment is contemplated in which an array of temperature sensors is positioned over the surface of heating element 310, being spaced apart to collect temperature readings. In such embodiments, the collected temperatures may enable an operator to determine any variability in electrical resistance of the heating wire. For instance, the temperature distribution collected by the array may be averaged to arrive at an average temperature. The heat generated by the heating element 310 may then be controlled so as to provide the average temperature.

Figure 4A:
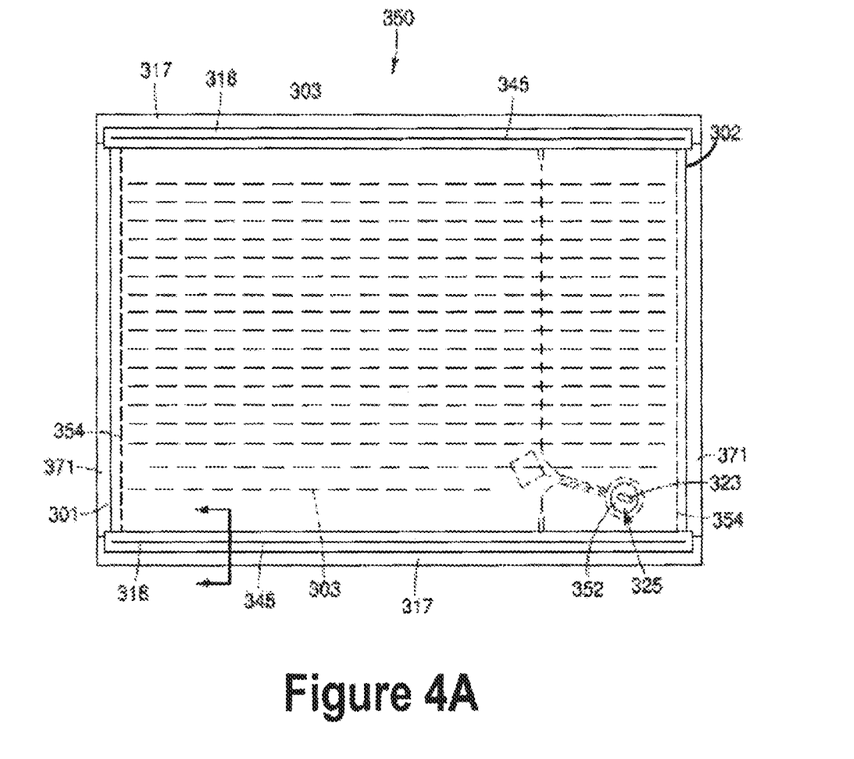
FIG. 4A is a top plan view of a heating element assembly, which may be incorporated in the blanket shown in FIG. 1.
Figure 4B:
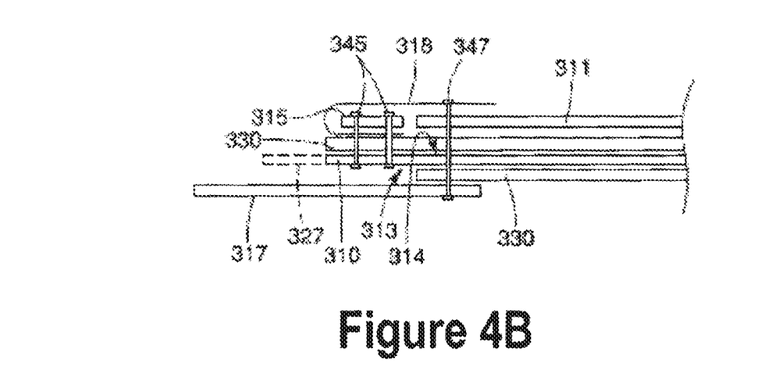
FIG. 4B is a cross-section view through section line 4B-4B of FIG. 4A.

FIGS. 4A-4B show a pair of securing strips 317 coupled to the heating element 310. Each strip 317 may extend laterally from and alongside respective lateral portions of heating element 310, parallel to electrical terminals 315. Each strip 317 can be coupled to a side 313 of heating element 310 via the respective row of non-conductive stitches 347. A second pair of securing strips 371 is shown in FIG. 4A. Each strip 371 may extend longitudinally from and alongside respective side edges 301, 302 of heating element 310. The strips 371 may be coupled thereto by a respective row of non-conductive stitches 354. Strips 371 may extend over layer 311 or beneath heating element 310. As shown, strips 317 extend over stitches 345 on side 313 of heating element 310. The strips 317 can act as a layer of insulation and can prevent shorting between portions of side 313 of heating element 310, for instance, if heating element 310 were to be folded over on itself along rows of stitches 345 that couple electrical terminals 315 to heating element 310. In some embodiments, strips 317 may alternately extend over insulating members 318 on the opposite side of heating element 310. In certain embodiments, strips 317 and 371 are made of a polymer material (e.g., PVC or urethane). They may be heat sealed between one or more sheets of shell 105 (best seen in FIG. 1) in order to secure heating element assembly 350 within a gap between the two sheets of shell 105. According to an alternate embodiment, for example, shown by dashed lines in FIGS. 2A and 4B, heating element 310 extends laterally out from each electrical terminal 315 to an edge 327, which may include one or more slots or holes 307 extending therethrough so that inner surfaces of sheets of shell 105 (best seen in FIG. 1) can contact one another to be sealed together and thereby hold to edge 327.

Figure 5A:
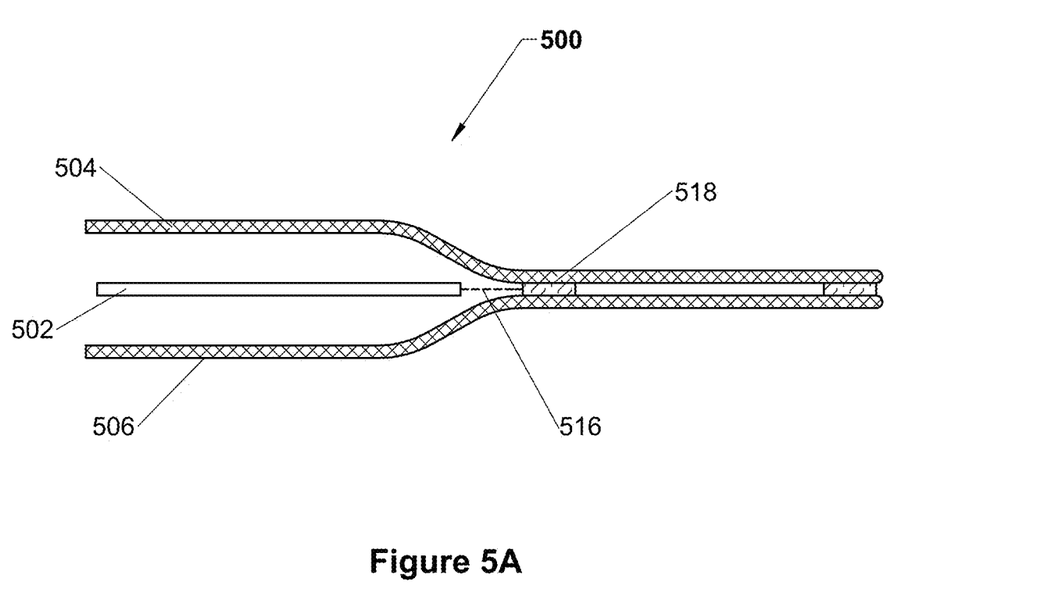
FIG. 5A is a cross-section of a shell containing a heating element according to some embodiments of the present invention.

FIG. 5A is a cross-section of a shell 514 containing a heating element 502 in accordance with some embodiments of the invention. The shell 514 can include a first sheet 504 and a second sheet 506 that are welded or bonded at one or more locations as will be described below. The sheets 504, 506 may define a pocket or pouch 508 that can enclose the heating element 502. As seen in FIG. 5A, first sheet 504 and second sheet 506 can be positioned on opposing sides of heating element 502 to envelope the heating element. As shown in the embodiment of FIG. 5A, the sheets are positioned so that the weldable layers 510, 512 of each sheet oppose each other. Any type of suitable weld may be used, such as heat welding (heat bonding), radiofrequency welding, ultrasonic welding, etc., depending on the type of materials used in sheets 504, 506. Alternately, adhesive bonding or sewing may be used. Each sheet 504 and 506 can have elastic properties and include substantially liquid-resistant materials. The sheets 504, 506 may have the ability to be welded together. In some embodiments, the liquid-resistant material includes a single layer, and in some embodiments, sheets are comprised of a laminate of two or more layers. For instance, in some embodiments one or both of sheets 504, 506 are comprised of a single layer of polyvinyl chloride (PVC) or urethane. In such embodiments where PVC or urethane is used, radiofrequency welding, ultrasonic welding or heat sealing may be used to bond the sheets 504, 506 together. PVC sheets also provide a liquid-resistant material in order to protect the heating element 502 from fluids to which the heating blanket is exposed.

Figure 5B:
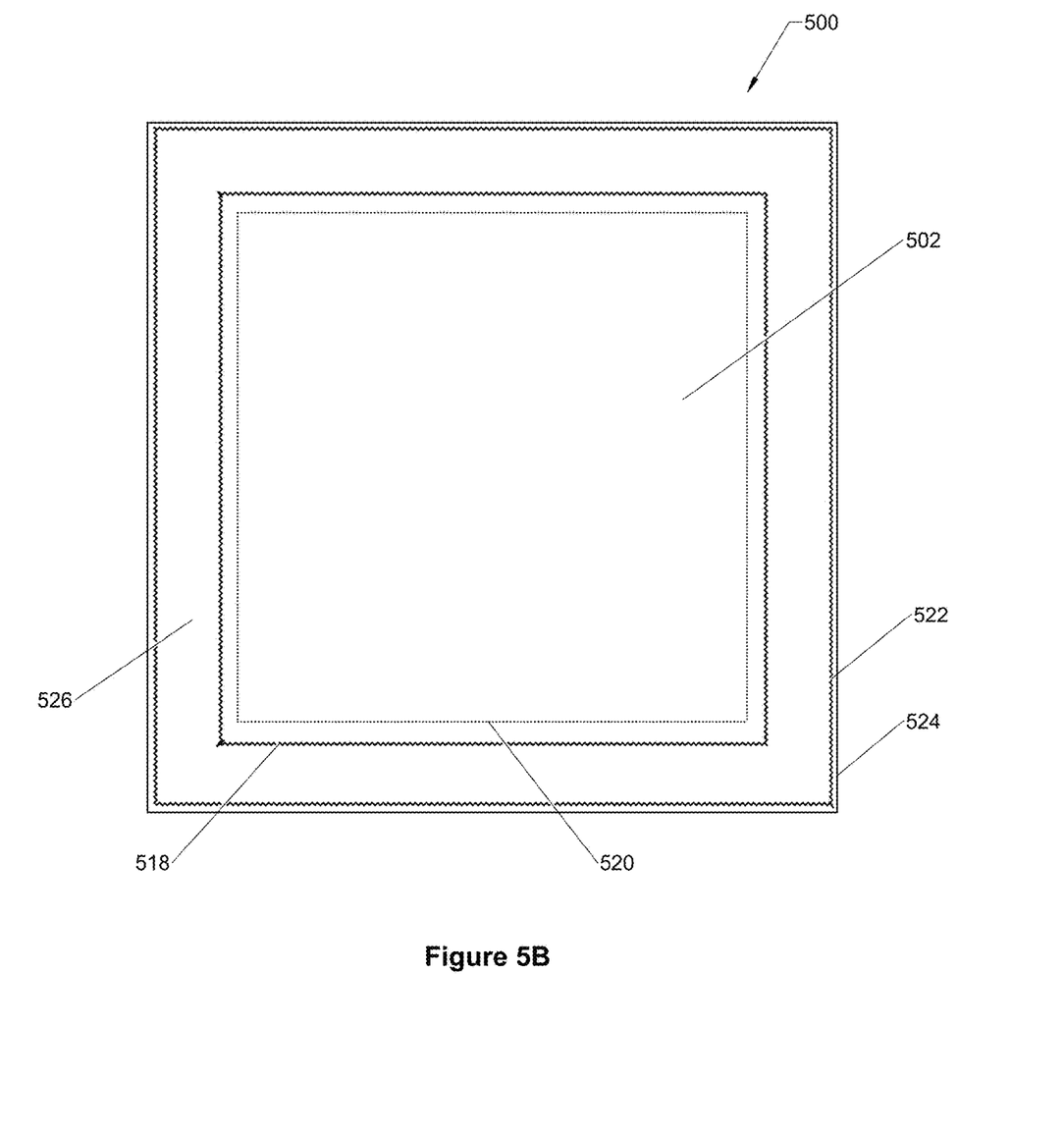
FIG. 5B is a top plan view of the shell of FIG. 5A.

FIG. 5B is a top plan view of the heating blanket 500 depicted in FIG. 5A. In some embodiments, the sheets 504, 506 are sized to completely cover the heating element 502, and can extend beyond all edges (e.g., first, second, third and fourth edges in FIG. 5B) of the heating element 502. In some embodiments, the heating element 502 is substantially hermetically sealed into the shell 514 formed by the two sheets 504, 506. As shown in the embodiment of FIGS. 5A and 5B, the sheets 504, 506 are coupled together along two welds. A first weld 518 can extend about a perimeter 520 of the heating element 502, thus surrounding the entire periphery of the heating element. The perimeter 520 may be formed by the first, second, third and fourth edges of the heating element. A second weld 519 can extend about a perimeter 524 of the sheets 504, 506, thus sealing the periphery of the sheets 504, 506 together. While the exemplary embodiment discloses welding, any other bonding means known in the art can be employed instead of or in addition to the first and second welds 518, 519. In some embodiments, the space 526 between the first weld 518 and the second weld 519 may be totally or partially welded together. In alternate embodiments, the space 526 between the welds may contain other structural components of the blanket as previously described and further discussed below. For example, the space 526 can enclose weighting members, the added weight of which may retain the blanket in position and against the patient.

As previously discussed with reference to at least FIGS. 2A, 4A and 4B, securing strips 317, 371 or securing edges 327 can be provided in some embodiments to facilitate securing the heating element to the shell 500. With reference to FIG. 8, an exemplary securing strip 516 can comprise a weldable plastic film (e.g., urethane). A first end of the securing strip 516 can be attached to the heating element 502, for example by sewing. A second end of the securing strip 516 (or securing edge according to alternate embodiments) can be placed between the two sheets 504, 506 and incorporated into the welds between the two sheets. Thus the heating element 502 is held in an extended position within the shell 500, without using stitches, rivets or grommets or other means that may pierce the flexible material sheets and make the shell difficult to clean.

Some embodiments incorporate one or more wires (or metal strips or other similar elongated members that can be bent into any position and hold that position) into the electric blanket to help secure and position the blanket. The wires may have malleable properties that facilitate bending and/or wrapping around the patient in order to secure the blanket so that the blanket may conform closely to the patient. The wire may have malleability that allows the wire to be bent into any shape. The wire can be made of copper. Other metals such as aluminum may be used. The wire can be multistranded or single stranded. Wires shaped like rods are also anticipated. The wire may be coated in plastic to form rounded plastic tips that prevent the wire ends from piercing through the flexible polymeric film sheaths that are securing the wire in the blanket.

Figure 6:
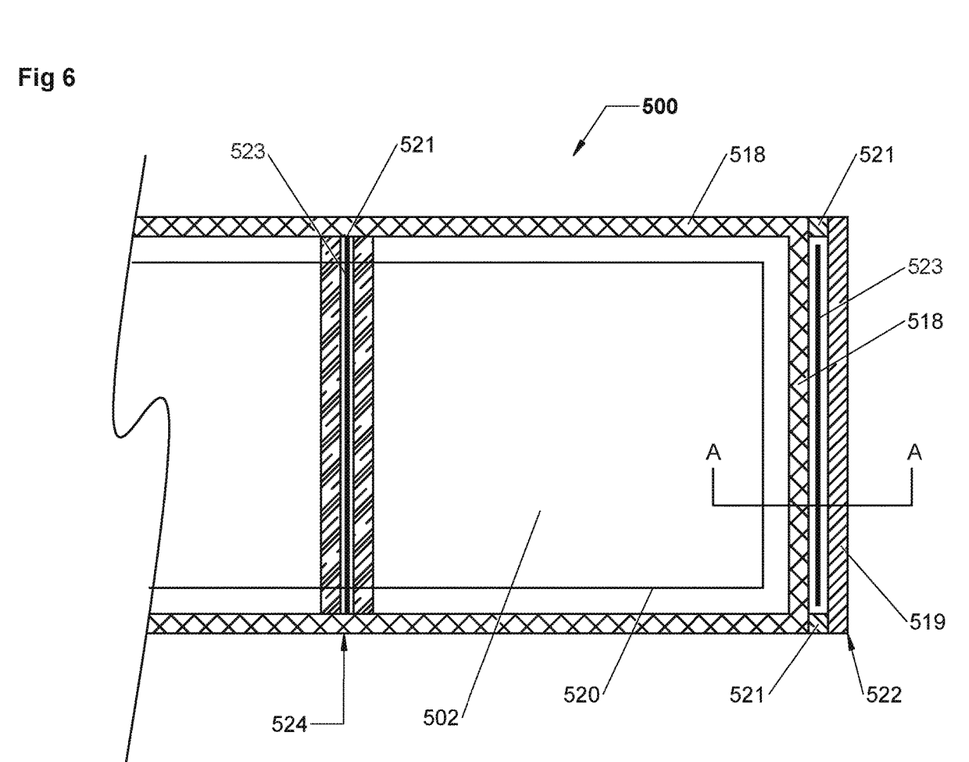
FIG. 6 is a top plan view of a heating blanket containing malleable wires.
Figure 7:
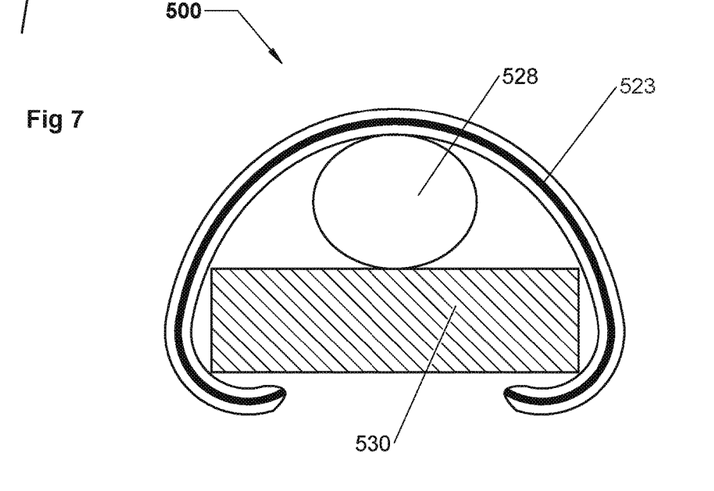
FIG. 7 is a cross-section view of a heating blanket containing a malleable wire.

As shown in FIG. 6, the one or more wires 523 extend substantially from one edge (e.g., first edge) within space 521 of the warming blanket to the opposing edge (e.g., second edge). The wire 523 may be located near an edge 522 of the blanket 500 or in a central region 524 (best seen in FIG. 6). FIG. 7 shows the cross section of a patient's arm 528 resting on the arm board 530 of the surgical table. As shown, the wire 523 wraps the heated blanket 500 around the arm 528 and arm board 530, improving conductive heat transfer and anchoring the blanket in place.

Figure 8A:
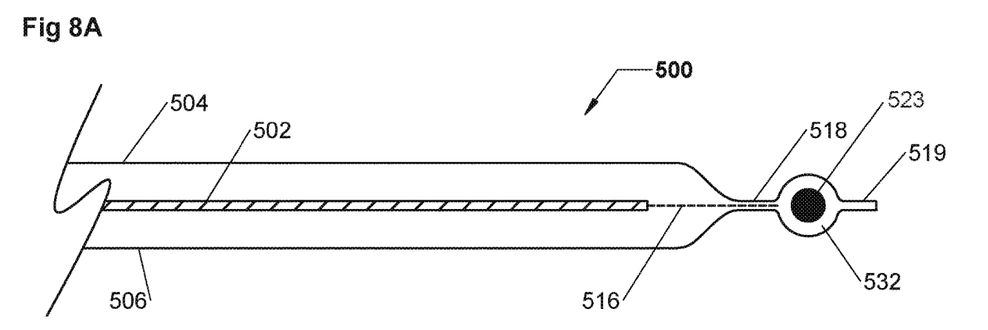
FIGS. 8A-E are cross-section views through section line A-A of FIG. 6 of a heating blanket containing a malleable wires.

The wire 523 can be incorporated into the shell 514 of the heating blanket 500. In FIGS. 6 and 8A, the shell 514 covering the heating element 502 can be made of two sheets of flexible polymeric film material 504, 506. The first bond 518 couples the two sheets 504, 506 as described previously. The second bond 519 may couple the two sheets of a portion of the perimeter of the shell 514 as described previously. An elongate space 521 that acts as a sheath 532 may be formed between the two parallel bonds 518, 519. The wire 523 can be inserted into and sealed into the elongate sheath 532 by welding/bonding the ends, securing it in position along and near one edge of the blanket.

Figure 8B:
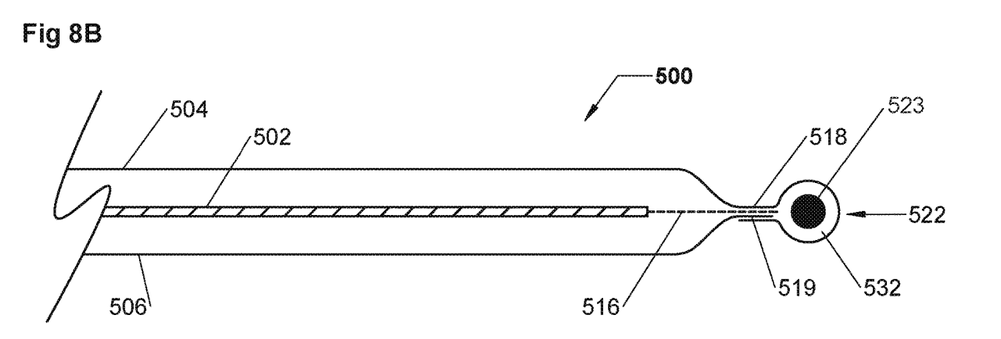
Figure 8C:
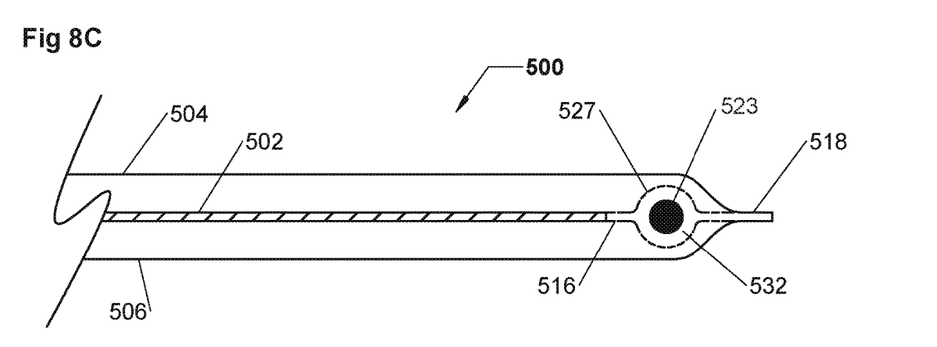

In some embodiments, as shown in FIG. 8B, one of the sheets 504 may be wrapped around the wire 523 at the edge 522 and then welded/bonded back on itself to create an elongate sheath 532 for securing the wire 523 when the ends of the sheath 532 are welded/bonded. This design may result in a rounded edge rather than sharp edge as seen in FIG. 8A.

In some embodiments, as shown in FIG. 8B, one of the sheets 504 may be wrapped around the wire 523 at the edge 522 and then welded/bonded back to the other sheet 506 (or on itself) to create an elongate sheath 532 for securing the wire 523 when the ends of the sheath 532 are welded/bonded. This design may result in a rounded edge rather than sharp edge as seen in FIG. 8A.

Figure 8D:
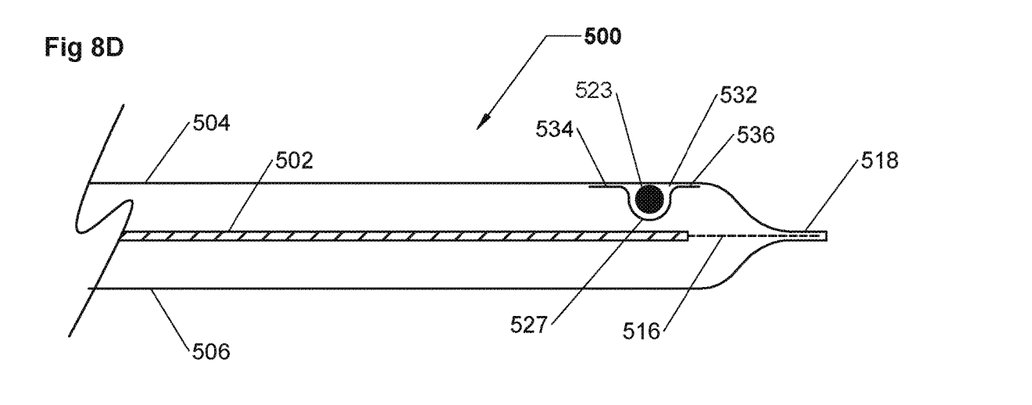

In some embodiments, as shown in FIG. 8D, the wire 523 can be inserted into an elongate sheath 532 formed of a fabric or a film. The sheath 532 can be welded or bonded to the shell 514. In this example, the film or fabric forming the elongate sheath 532 is welded or bonded along two bond lines 534, 536 to the sheet 504 of the shell 514, creating an elongate sheath 532 between the weld or bond lines 534, 536, into which the wire 523 can be secured. Other methods of securing the wire or wires to the blanket such as sewing or bonding via an adhesive are anticipated. Further, any type of welding disclosed herein such as heat welding, radiofrequency welding or other bonding methods known in the art such as adhesive bonding and sewing can be used.

Figure 9:
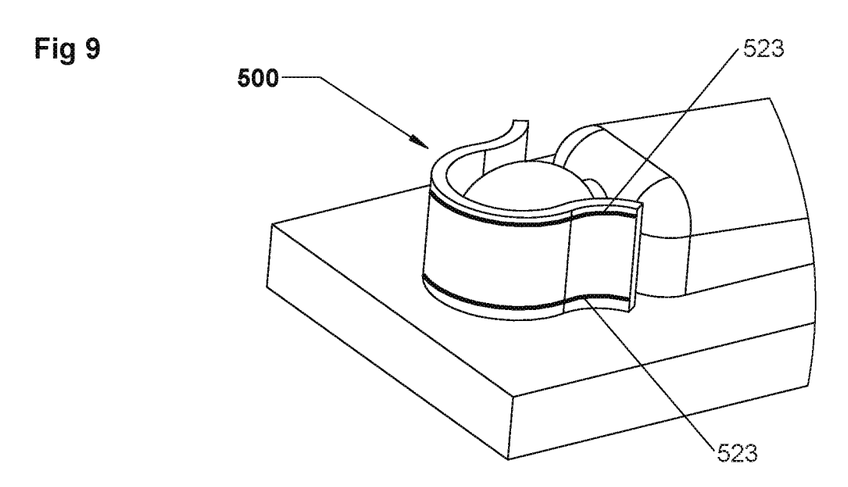
FIG. 9 is a prospective view of a pediatric patient lying on an operating table.
Figure 10:
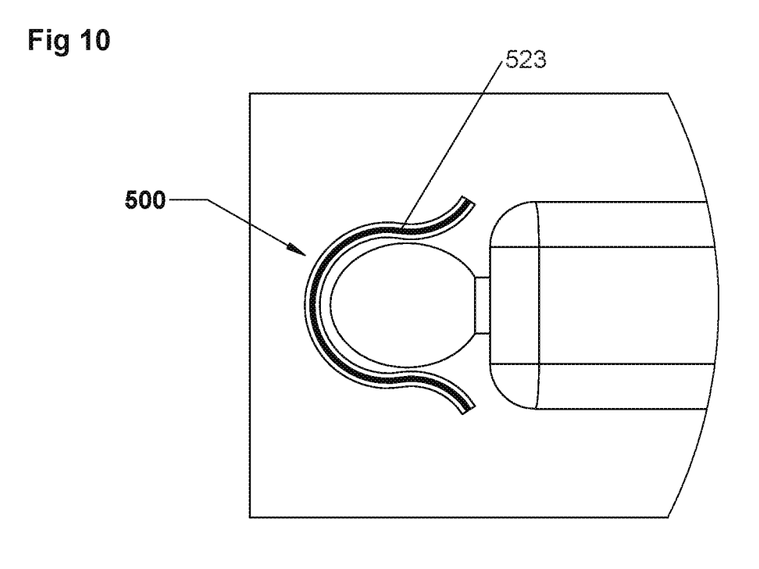
FIG. 10 is a top view of a pediatric patient lying on an operating table.

There are many examples of how the wire or wires may be used in heating blankets. For example, if the blanket is designed to cover the patients' outstretched arms as they lay on an operating table, the wire may be located at edges of the blanket near the patients' hands. As shown in FIG. 7, the wire 523 in this location can be wrapped around the patients' wrists 528 or around the end of the arm board 530, to secure the blanket in place on the outstretched arms. Not only does the wire 523 keep the blanket 500 from shifting off of the patient but it also holds the heating element 502 in close contact with the arms, improving the conductive heat transfer to the patient. Another exemplary embodiment is shown in FIGS. 9 and 10, where a pediatric patient may have a blanket such as those described elsewhere herein wrapped around the patient's head during surgery. The wires 523 may prevent the blanket 500 from losing contact with the patient's head and improve conductive heat transfer due to better contact between the patient's head and the blanket.

In some embodiments, a small heated blanket that may be designed to wrap around the patient's head while the patient lies supine on the operating table. In this case, the blanket may be oriented vertically and may be positioned on the one side of the patient's head. The blanket may then wrap around the top of the patient's head and covers the other side of their head forming at least a portion of a "U" shape. The wire may be incorporated into one or more edges of the blanket. The wires can be bent into at least a portion of a "U" shape which naturally holds the blanket in position around the patient's head. While an exemplary shape forming attribute of the blanket is disclosed, the particular shape into which the wire may be bent do not limit the scope of the invention.

Figure 8E:
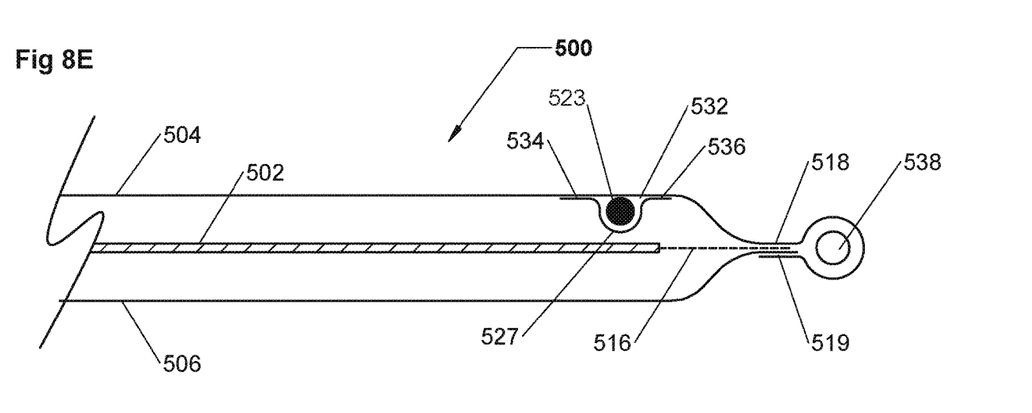

In some embodiments, a piping or tubing can be molded to the edge of the blanket 500 as shown in FIG. 8E. The tube 538 may be placed between the two sheets 504, 506 at their edges or one or more of the edges of the sheets 504, 506 may be wrapped around the tubing as shown in FIG. 8E. Exemplary materials for the tube may include plastic or another suitable material. The tube may seal the edges of the shell and create a rounded edge to the warming blanket. In some embodiments, the tube can be plastic tubing such as PVC tubing that is between 1/8 and 3/8 inches in inner diameter.

The tube at the edge of the blanket may soften the edge to improve patient comfort when the blanket contacts the patient.

The blankets according to embodiments of the invention offer one or more advantages. The heating element of the blanket made of fabrics with elastic properties may have durability and improved mechanical strength even when folded or stretched repeatedly. The blanket may be liquid-resistant, chemical-resistant and protect a patient from electrical shock hazards. The blanket has the ability to deform into a compound curve. Wires with malleability allow the blanket to secured or wrapped around a patient's body or a portion of the patient's body without the need for any securing or fastening mechanism. Such embodiments may improve heat transfer between the blanket and the patient, ultimately providing improved patient compliance in a safe and effective manner.

In the foregoing detailed description, the invention has been described with reference to specific embodiments. However, it may be appreciated that various modifications and changes can be made without departing from the scope of the invention as set forth in the appended claims. Although embodiments of the invention are described in the context of a hospital operating room, it is contemplated that some embodiments of the invention may be used in other environments. Those embodiments of the present invention, which are not intended for use in an operating environment and need not meet stringent FDA requirements for repeated used in an operating environment, need not including particular features described herein, for example, related to precise temperature control. Thus, some of the features of some embodiments described herein are not necessarily included in some embodiments of the invention which are intended for alternative uses.

What is claimed is:

1. A heating blanket, comprising:
   a heating element including a first edge, a second edge, a third edge, and a fourth edge, the first, second, third, and fourth edges forming a first perimeter of the heating element, the heating element disposed in the shape of a sheet;
   a shell covering the heating element and comprising at least a first sheet and a second sheet of polymeric material, the shell having a second perimeter defined by one or more edges;
   a pair of bus bars, each bus bar of said pair of bus bars being coupled to the heating element and extending between two edges of the heating element;
   a first weld coupling the first and second sheets of polymeric material together adjacent the first perimeter of the heating element;
   a securing strip securing the heating element to the shell, the securing strip comprising a first end secured to the heating element and a second end incorporated into the first weld; and
   one or more wires extending from a first edge of the heating blanket to an opposing edge of the heating blanket, each of the one or more wires extending only in a direction between the first edge of the heating blanket and the opposing edge of the heating blanket and secured within the heating blanket, each of the one or more wires being separate from the heating element, each of the one or more wires being electrically isolated from the heating element, each of the wires having malleable properties such that each of the wires is bendable into a shape and configured to hold that shape to allow the heating blanket to be secured to a patient, the bendability and shape retention of each wire of the one or more wires permitting the heating blanket to be held in contact with at least a portion of the patient, each of the one or more wires extending perpendicular to said pair of bus bars.

2. The heating blanket of claim 1, wherein the first weld is one of a radiofrequency weld, ultrasonic weld, or a heat weld.

3. The heating blanket of claim 1, further comprising:
   wherein at least one of the first sheet and the second sheet of polymeric material extends beyond the first weld and is wrapped back and bonded via a second bond to form an elongate sheath between the first weld and the second bond along an edge of the shell; and
   one or more tubes inserted into the elongate sheath before sealing an end of the elongate sheath shut to form a rounded edge.

4. The heating blanket of claim 3, wherein the one or more tubes are PVC tubes.

5. The heating blanket of claim 3, wherein at least a portion of the heating element is coated with a liquid-resistant elastomeric material.

6. The heating blanket of claim 1, wherein the one or more wires comprise at least two wires not interconnected to each other.

7. The heating blanket of claim 1, wherein the one or more wires extend past the first edge and the second edge of the heating element.

8. The heating blanket of claim 1, wherein each wire of the one or more wires extends only along a direction that is parallel to the first edge and the second edge of the heating blanket.

9. A heating blanket, comprising:
   a heating element including an opposing first edge and second edge, and an opposing third edge and fourth edge, the first, second, third and fourth edges forming a perimeter of the heating element, the heating element disposed in the shape of a sheet;
   a shell covering the heating element and comprising at least a first sheet and a second sheet of polymeric material, the shell having a perimeter defined by one or more edges;
   a pair of bus bars, each bus bar of said pair of bus bars being coupled to the heating element and extending between two edges of the heating element;
   a first bond coupling the first and second sheets of polymeric material together adjacent the perimeter of the heating element;
   a securing strip securing the heating element to the shell, the securing strip comprising a first end secured to the heating element and a second end incorporated into the first bond; and
   one or more wires extending from a first edge of the heating blanket to an opposing edge of the heating blanket, each of the one or more wires extending only in a direction between the first edge of the heating blanket to the opposing edge of the heating blanket and secured within the heating blanket, each of the one or more wires being separate from the heating element, each of the one or more wires being electrically isolated from the heating element, each of the wires having a malleable properties such that each of the wires is bendable into a shape and configured to hold that shape to allow the heating blanket to be secure to a patient, each wire of the one or more wires permitting the heating blanket to be held in close contact with at least a portion of the patient, each of the one or more wires extending perpendicular to said pair of bus bars.

10. The heating blanket of claim 9, wherein the heating element comprises a conductive or semi-conductive fabric or a conductive or semi-conductive film.

11. The heating blanket of claim 10, wherein the conductive or semi-conductive fabric or the conductive or semi-conductive film is polypyrrole.

12. The heating blanket of claim 9, wherein the shell comprises PVC or urethane.

13. The heating blanket of claim 9, wherein the shell comprises a polymer bonded to a fabric.

14. The heating blanket of claim 9, wherein the first bond is one of a radiofrequency bond, ultrasonic bond, a heat bond, or an adhesive bond with or without stitching reinforcement.

15. The heating blanket of claim 9, wherein a second bond is formed between the first sheet and the second sheet of polymeric material, adjacent the perimeter of the shell and parallel to the first bond, the second bond creating an elongate sheath along at least an edge of the shell, wherein the one or more wires is inserted into the elongate sheath before sealing an end of the elongate sheath shut.

16. The heating blanket of claim 15, wherein a strip of polymeric film or fabric is bonded within the first and second bonds to secure the strip of polymeric film at the edge of the shell, forming the elongate sheath adjacent the perimeter of the shell; and the one or more wires are inserted into the elongate sheath before sealing the end of the elongate sheath shut.

17. The heating blanket of claim 9, wherein at least the first sheet of polymeric material extends beyond the first bond, the first sheet being wrapped back and bonded to form an elongate sheath adjacent the perimeter of the shell, wherein the one or more wires are inserted into the elongate sheath before sealing an end of the elongate sheath shut.

18. The heating blanket of claim 9, wherein a strip of polymeric film or fabric is bonded with at least one of the first sheet and the second sheet of polymeric material, forming an elongate sheath, the elongate sheath having at least one end, wherein the one or more wires is inserted into the elongate sheath before sealing the an end of the elongate sheath shut.

19. The heating blanket of claim 9, wherein at least a portion of the heating element is coated with a liquid-resistant elastomer.

20. The heating blanket of claim 19, wherein the liquid-resistant elastomer is silicone rubber.

21. The heating blanket of claim 9, wherein each of the wires is made of copper or aluminum.

22. The heating blanket of claim 9, wherein each of the one or more wires is multi-stranded.

23. The heating blanket of claim 9, wherein each of the one or more wires is single stranded.

24. The heating blanket of claim 9, wherein each of the one or more wires is coated with a plastic coating, to form rounded plastic tips, the rounded plastic tips configured for covering one or more ends of each of the one or more wires.

* * * * *